United States Patent [19]

McCormick

[11] Patent Number: 5,269,671

[45] Date of Patent: Dec. 14, 1993

[54] APPARATUS FOR EMBEDDING TISSUE SAMPLES

[76] Inventor: James B. McCormick, 6755 Longmeadow Dr., Lincolnwood, Ill. 60646

[21] Appl. No.: 833,909

[22] Filed: Feb. 11, 1992

[51] Int. Cl.⁵ ..................... C12M 1/16; B22D 19/00
[52] U.S. Cl. ..................... 425/117; 249/83; 249/96; 422/99; 422/102; 425/125
[58] Field of Search ............ 425/117, 125; 427/4; 249/83, 96; 422/99, 101, 102; 206/560, 564, 565, 591; 220/408, 410, 413, 400; 435/299

[56] References Cited

U.S. PATENT DOCUMENTS

| | | | |
|---|---|---|---|
| 3,674,396 | 7/1972 | McCormick | 425/117 |
| 3,982,862 | 9/1976 | Pickett et al. | 425/117 |
| 4,483,442 | 11/1984 | Worth | 206/560 |
| 4,501,363 | 2/1985 | Isbey, Jr. | 206/560 |
| 4,557,903 | 12/1985 | McCormick | 422/101 |
| 4,569,647 | 2/1986 | McCormick | 425/117 |
| 4,623,308 | 11/1986 | Hellon | 425/117 |
| 4,684,013 | 8/1987 | Jacobs | 206/560 |
| 4,801,553 | 1/1989 | Owen et al. | 425/117 |
| 4,833,819 | 5/1989 | Sherman | 206/560 |
| 5,080,869 | 1/1992 | McCormick | 422/102 |

Primary Examiner—Robert J. Warden
Assistant Examiner—L. M. Crawford
Attorney, Agent, or Firm—Fitch, Even, Tabin & Flannery

[57] ABSTRACT

The present invention is directed to a system for providing an embedded tissue specimen subsequent to fluid treatment of the specimen and preparatory to histological examination. The system includes the combination of a cassette for use in the preparation of tissue specimens for histological examination and an embedding mold having a first cavity for receiving the treated specimen and a second cavity for receiving the cassette in an interlocked position overlying the first cavity.

1 Claim, 2 Drawing Sheets

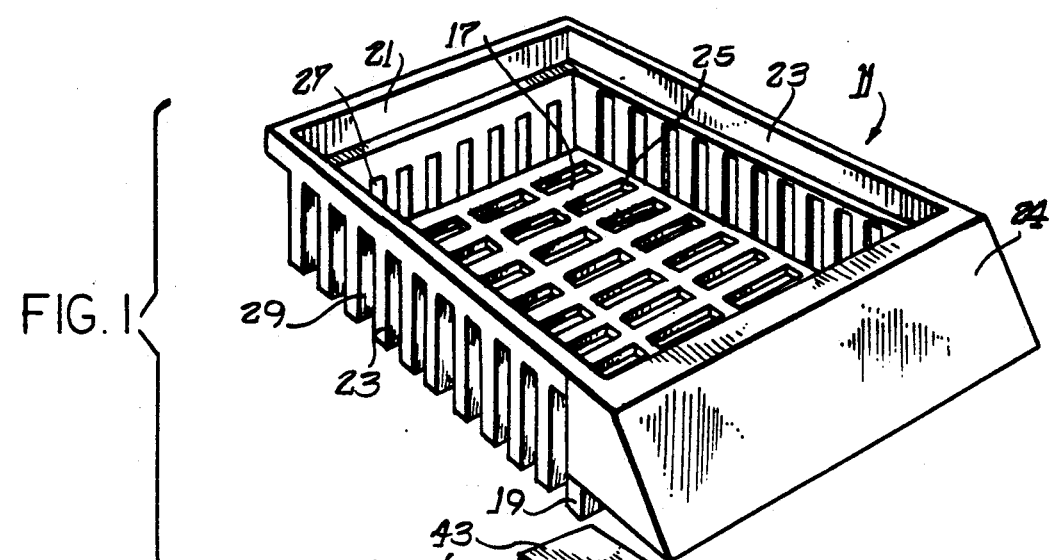
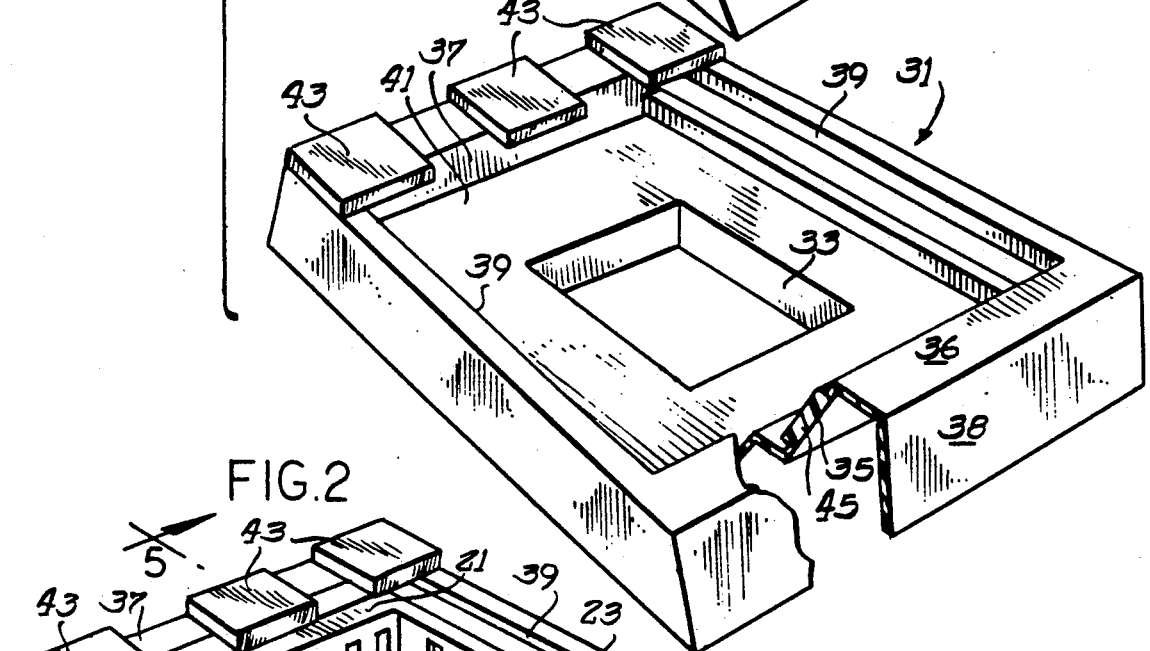
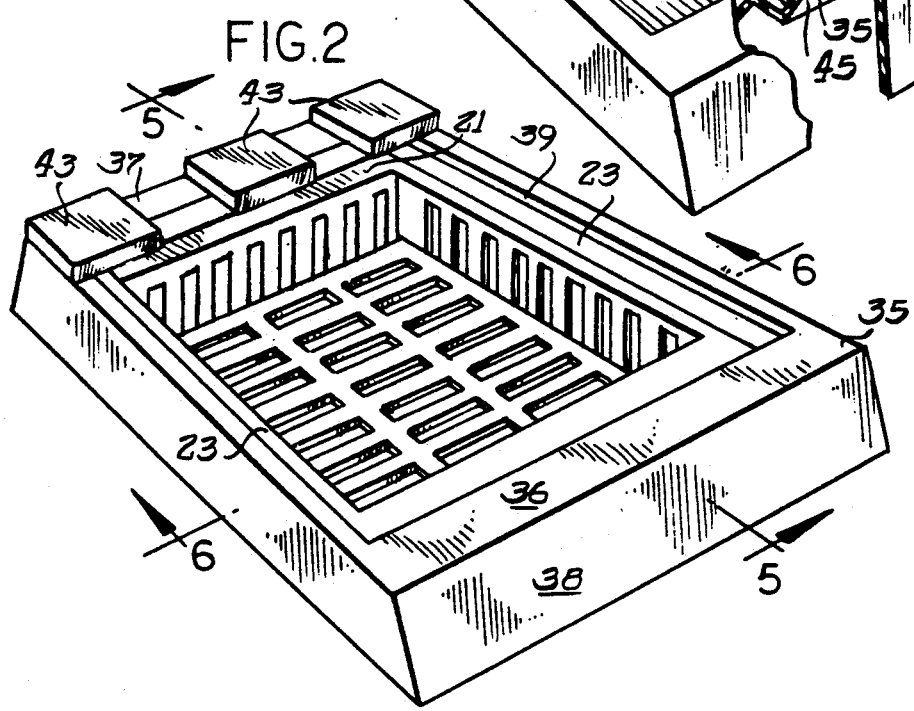

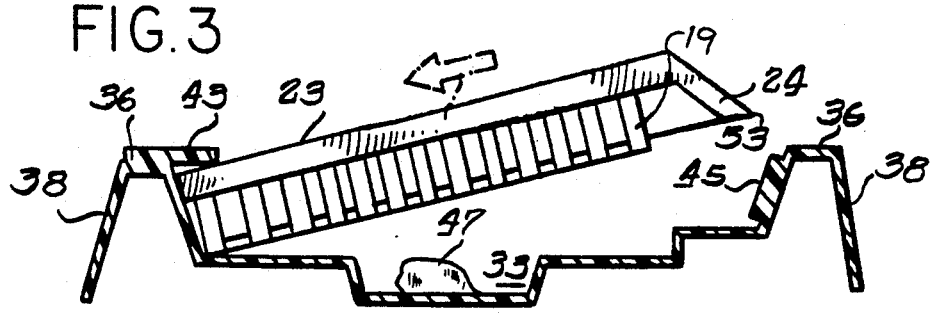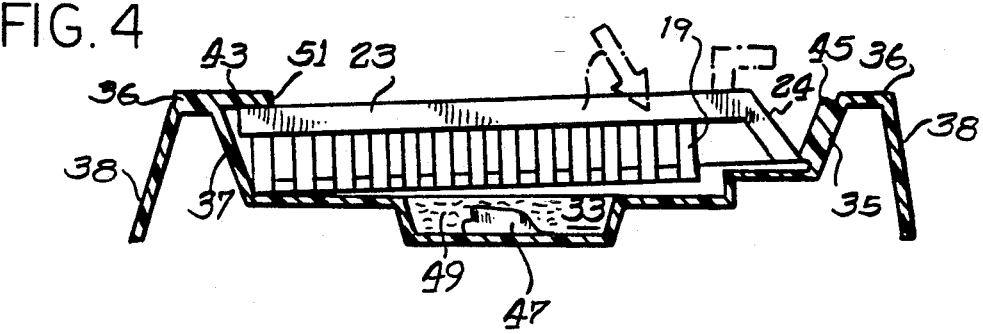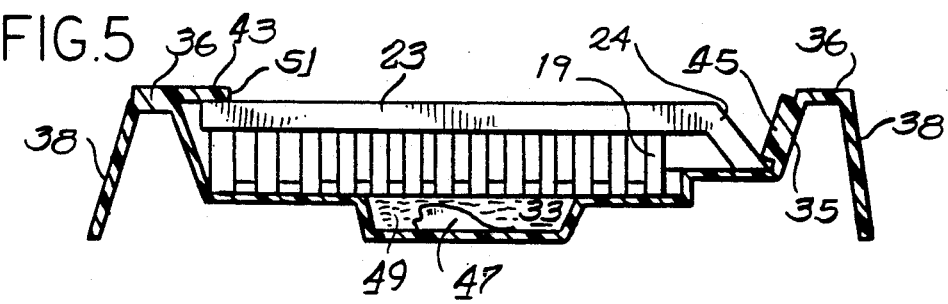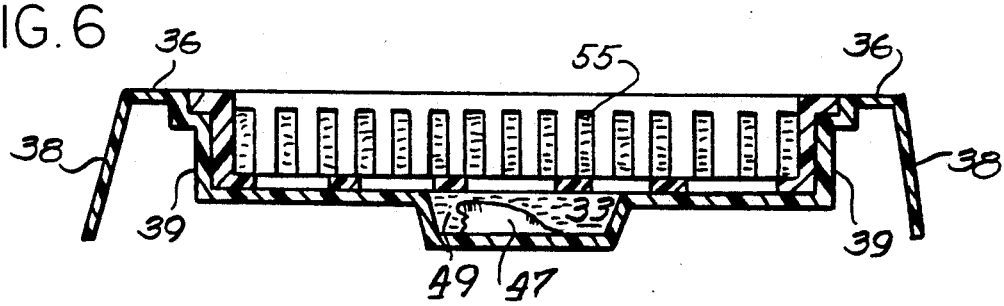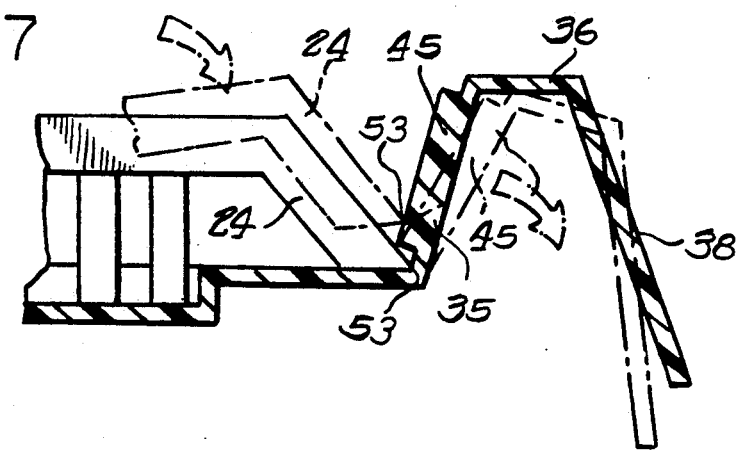

APPARATUS FOR EMBEDDING TISSUE SAMPLES

FIELD OF THE INVENTION

The present invention relates to embedding tissue samples for histological examination and, more particularly, relates to improved methods and apparatus for embedding tissue samples which have been treated by various fluids prior to embedding the tissue samples in paraffin or the like in preparation for microtome slicing and microscopic examination.

BACKGROUND OF THE INVENTION

Standard procedures for preparing tissue samples for microscopic examination involve embedding the tissue sample in paraffin and slicing the paraffin-embedded tissue sample very thinly with a microtome. Prior to embedding the tissue sample, the tissue sample is pretreated in various solutions appropriate to the examination. Typically, prior to paraffin embedding, the tissue sample is fixed, dehydrated, cleared, infiltrated with molten paraffin and, depending on the test, stained. Such prior treatment of the tissue sample requires subjecting the tissue sample to contact with various fluids, including ethanol, xylene, formaldehyde and water.

A histology laboratory processes a large number of tissue samples for examination and it is important that the tissue samples be prepared as efficiently as possible. A large variety of apparatus has been developed to improve the efficiency of the preparation process. For example, U.S. Pat. No. 3,674,396 to McCormick discloses capsules in which a tissue sample is both prepared for embedding through exposure to various solutions and is then embedded in proximity to the capsule. The '396 McCormick patent discloses a process wherein the tissue sample is statically exposed to the various fluids required for preparation of the tissue samples. In the capsules of the '396 McCormick patent, perforated bottom walls are used to retain the tissue samples while providing access to the tissue samples of the various solutions and finally to molten paraffin.

In previous procedures for processing the tissue sample after subjecting the tissue sample to the various fluids required to treat the sample, the treated tissue sample is removed from the capsule or cassette and is placed into the well of a mold. Molten embedding material is then poured over the tissue sample. The cassette used to process the tissue sample is then placed over the well in the mold and additional molten embedding material is poured into the cassette. After the embedding material solidifies, a cast block is formed that includes the capsule as its base and a protruding portion having the tissue specimen disposed adjacent its front surface. In accordance with standard procedure, the size of various cassettes and capsules which have been developed for processing tissue sample, has been relatively standardized so that the cassette or capsule can be used as the chuck in a microtome slicing device.

U.S. Pat. No. 5,080,869 to McCormick describes a particularly useful cassette for processing tissue samples in a highly efficient manner. The cassette of the '869 McCormick patent is stackable and can be used for preparing a plurality of specimens. The cassette generally includes a plurality of apertures disposed in the walls of the cassette for passage of processing fluids in a direction both orthogonal and parallel to the plane of the bottom wall of the cassette. The cassette also includes a sloping extension of the front wall of the cassette for ease in placing indicia on the cassette for identification of the sample.

It would be desirable to provide an embedding mold for use with the cassette of the type disclosed in the '869 McCormick patent which facilitates embedding the processed tissue sample without incurring problems of previous tissue processing capsules and cassettes wherein the capsule or cassette is placed loosely in an embedding mold and movement of the cassette can occur causing wax to overrun the sides of the cassette. Such excess wax must be flash trimmed to conform the shape of the cassette to the chuck of the microtome which holds the cassette and specimen for cutting. Precision casting would save technical time and improve function.

For example, U.S. Pat. Nos. 4,557,903 and 4,569,647, both to McCormick, disclose improved apparatus for preparing and embedding tissue samples for histological examination. In the '903 McCormick patent, a tissue specimen processing capsule is provided which includes a pair of interlocking frames, each of the frames having a porous web spread across its central opening for holding a tissue specimen in a region divided between the webs. The porous webs permit access to the specimen by processing and impregnating fluids. After the tissue specimen is processed, it is removed from the capsule and placed in a depression of a mold. The empty capsule is placed over the mold depression containing the tissue specimen. Molten paraffin is poured into the mold to fill the depression and to cover the tissue specimen and the porous material of the capsule. The molten paraffin solidifies to form a tissue block with the capsule serving as a clampable base for an outwardly extending, tissue-containing portion.

The '647 McCormick patent discloses an improved method for contacting a tissue specimen with a fluid which is used to treat the tissue specimen. In the '647 McCormick patent, capsules for processing and embedding tissue samples each include a mold, which provides a cavity to receive the tissue sample. The mold has an upper end and a porous or non-porous bottom. The capsule further includes a cover which fits over the open upper end of the mold. The cover includes a frame on which is located a web of porous material intermediate the top and bottom of the frame so that the cover is provided with a recess. The porous web provides access to tissue processing liquids and liquid tissue embedding material, such as paraffin, but prevents passage of any small portions of the tissue specimen which may be generated, thereby preventing cross-contamination of individually capsuled and jointly processed tissue samples. After the tissue samples have been treated with the required fluids, the cover recess above the porous web is at least partially filled with molten paraffin embedding material so that when the embedding material solidifies, the porous web is embedded and the solidified material is thereby formed into a block in the mold. With the porous web and the tissue sample mutually embedded in the block of solidified paraffin, the block is removed from the mold and the cover may be clamped in a microtome and sliced by a microtome blade.

While apparatus and methods for preparing and embedding tissue samples for histological examination have progressed over the years to provide more efficiency in the preparation of tissue specimen, the large number of tissue samples which are prepared daily by histological laboratories, require the most efficient techniques available to increase the number of samples that can be processed and to reduce the cost of such processing.

Accordingly, it is the principal object of the present invention to provide apparatus for use in embedding tissue specimen for histological examination which increases the efficiency of the embedding operation of a specimen and which reduces the cost of preparing tissue samples for microtome slicing and treatment.

Another object of the present invention is to provide an embedding mold for utilization with a cassette to operate in cooperation with such cassette to provide an improved embedding technique.

These and other objects of the invention will become more apparent from the following detailed description and the accompanying drawings.

BRIEF DESCRIPTION OF THE DRAWINGS

FIG. 1 is a perspective view of the cassette of the invention and the embedding mold for use with the cassette;

FIG. 2 is a perspective view of the cassette shown inserted into the embedding mold;

FIG. 3 is a side view taken along line 5—5 of FIG. 2 showing the cassette in partial engagement with the embedding mold;

FIG. 4 is a side view taken along line 5—5 of FIG. 2 showing the cassette in eminent engagement with the embedding mold;

FIG. 5 is a side view taken along line 5—5 of FIG. 2 showing the cassette in engagement with the embedding mold;

FIG. 6 is a cross-sectional view taken along line 6—6 of FIG. 2 showing the close tolerances which exist between the cassette and the embedding mold, particularly at the side walls of the cassette; and FIG. 7 is a greatly magnified view taken at section 7 of FIG. 5 showing the mechanism of the snap fit of the cassette with the embedding mold.

SUMMARY OF THE INVENTION

The present invention is directed to a system for providing an embedded tissue specimen subsequent to fluid treatment of the specimen and preparatory to histological examination. The system includes the combination of a cassette for use in the preparation of tissue specimens for histological examination and an embedding mold having a first cavity for receiving the treated specimen and a second cavity for receiving the cassette in an interlocked position overlying the first cavity.

DETAILED DESCRIPTION OF THE INVENTION

As shown in FIG. 1, the cassette 11 comprises a bottom wall 17, a front wall 19, a back wall 21 and two side walls 23. As best seen in FIG. 1 in combination with FIGS. 3-5, an inclined wall 24 extends in a forwardly and downwardly sloping direction from the top of the cassette and away from the front wall 19. The inclined wall 24 is a false wall that is used to facilitate the insertion of indicia on the face of the cassette.

The bottom wall is provided with a plurality of apertures 25. As shown in the embodiment in FIG. 1, the back wall 21 and front wall 19 are provided with apertures 27 and both of the side walls 23 are provided with apertures 29. The apertures are provided for the purpose of passing fluid through the cassette at a direction both parallel and orthogonal to the bottom wall 17, as described in the '869 McCormick patent.

An embedding mold 31 is also shown in FIG. 1. The embedding mold 31 has a well 33 for reception of specimen samples after they are processed in the cassette 11. The embedding mold 31 has a front wall 35, a back wall 37 and side walls 39. The back wall 37 and side walls 39 have inner surfaces which generally conform to the outer surface of the back wall and side walls of the cassette 11. The bottom wall 41 of the embedding mold 31 is flat to conform to the flat surface of the bottom wall of the cassette 11. The front wall 35 of the embedding mold, as best seen in FIG. 1, in combination with FIGS. 3-5, has a downwardly sloping surface in a rearward direction with respect to the forwardly, downwardly sloping direction of the inclined front wall of cassette 11. As best seen in FIG. 1, in combination with FIGS. 3-5, the embedding mold may also be provided with a peripheral rim 36 and surrounding skirt 38 providing support stability while manipulating the embedding mold.

Affixed to the top of back wall 37 are a series of retaining flanges 43. As explained in further detail hereinbelow, retaining flanges 43 serve to restrain the top of the back wall of the cassette 11 when it is positioned in the embedding mold and also serves as a fulcrum to assist in assembling the cassette 11 into the embedding mold 31.

The inner surface of the front wall 35 of the embedding mold has a resilient restraining strip 45, for engagement of the foremost tip of the front wall of cassette 11. Both the retaining flange 43 and the resilient restraining strip 45 can be provided as a single piece extending across the width of the back wall and front wall, respectively, or can be a series of pieces which extend only partially across the back wall and the front wall, respectively.

In operation, a treated specimen 47 is removed from the cassette 11 after treatment and is placed into the specimen well 33, as shown in FIG. 3. Molten embedding material is then poured around the specimen to a level sufficient to fill the specimen well 33. The cassette 11 is then slid into the embedding mold 31 at an angle, as shown in FIG. 3, so that the back wall of the cassette slides underneath the retaining flange 43.

As shown in FIG. 3, the point at which the forward edge 51 of the retaining flange 43 meets the side walls of the cassette 11 acts as a fulcrum to provide leverage for pushing the cassette 11 downwardly into mating engagement with the embedding mold 31. The use of the generation of force from the fulcrum effect permits tight clearances to be used between the outer walls of the cassette 11 and the inner walls of the embedding mold 31.

As shown in FIG. 4 and FIG. 7, as the forward lip 53 of the inclined wall 24 of the cassette meets the resilient restraining strip 45, pressure is exerted on the restraining strip 45 to move the restraining strip 45 out of the way of the forward lip 53 of the inclined wall 23. As shown in FIG. 5, as soon as the forward lip of the inclined wall 24 passes the bottom most edge of resilient restraining strip 45, the resilient restraining strip 45 snaps back into place to lock the cassette 11 into engagement with the embedding mold 31. As soon as the cassette 11 is placed into interlocking relationship with the embedding mold 31, additional molten embedding material 55 is poured into the cassette 11 to fill the cassette 11 with embedding material. The molten embedding material penetrates through the apertures in the bottom wall 17 of the cassette to engage the embedding material 49 filling the specimen well 33 so as to form an integral block of embedding material. Upon cooling, the embedding materials fill the cassette 11 and provide a protruding portion in the shape of the specimen well 33 which contains the specimen 47 in position for being sliced by a microtome into suitable specimen sizes.

Upon removing the cassette 11 from the embedding mold 31, the cassette 11, filled with embedding material, serves as the base of a specimen block which is insertable within a microtome block. A lifting tab 57, shown only in phantom outline in FIG. 4, can be provided to assist in removing the cassette 11 from the embedding mold 31. Slices can be shaved from the appended portion containing the specimen. The remainder of the cast block may be disposed of or may be stored so that, if reexamination of tissue or confirmation of results is required, additional slices may be shaved.

The specimen well 33, can, of course, be made of any suitable size for specimen examination. Typical sizes used for microtome slicing are 8×8 mm, 12×12 mm, 22×22 mm, 22×30 mm and 22×40 mm. The size of the specimen well is made to match the varied sizes of tissue samples which are typically examined.

While the invention has been described in terms of certain preferred embodiments, modifications obvious to one with ordinary skill in the art may be made without departing from the scope of the invention. Various features of the invention are set forth in the following claims.

What is claimed is:

1. A system for providing an embedded tissue specimen subsequent to fluid treatment and preparatory to histological examination, comprising a combination of a cassette for use in the preparation of tissue specimens for histological examination and an embedding mold having a first cavity for receiving a treated specimen and a second cavity for receiving said cassette, said cassette having a front wall, side walls, a back wall and a bottom wall, said bottom wall having a plurality of apertures, said cassette having a sloping false wall terminating in a front lip, said embedding mold having a front wall sloping away from said false wall, a resilient member affixed to said sloping front wall of said embedding mold for engagement with said front lip at the terminus of said sloping false wall of said cassette and said embedding mold having at least one flange affixed to the back wall for engagement of the back wall of said cassette, whereby when said cassette back wall is inserted under said embedding mold flange and said front lip of the terminus of said sloping false wall of said cassette is pressed under said resilient member, said cassette is placed in an interlocked position within said second cavity of said embedding mold and overlying said first cavity of said embedding mold.

* * * * *